United States Patent [19]

Uchida et al.

[11] Patent Number: 5,179,197
[45] Date of Patent: Jan. 12, 1993

[54] SECRETORY COMPONENT-CONTAINING COMPOSITION

[75] Inventors: Toshiaki Uchida, Kawagoe; Kaoru Sato, Kamifukuoka; Sunichi Dosako, Urawa; Chouemon Kanno, Utsunomiya; Norihiro Azuma, Utsunomiya; Hitoshi Kuriki, Utsunomiya, all of Japan

[73] Assignee: Snow Brand Milk Products Company, Ltd., Hokkaido, Japan

[21] Appl. No.: 669,089

[22] Filed: Mar. 15, 1991

[30] Foreign Application Priority Data

Mar. 15, 1990 [JP] Japan .................................. 2-065489
Feb. 21, 1991 [JP] Japan .................................. 3-049162

[51] Int. Cl.$^5$ ...................... C07K 15/14; A61K 35/20
[52] U.S. Cl. ................................ 530/366; 530/387.1; 530/413; 530/416; 530/833; 530/388.2; 530/861
[58] Field of Search ............... 530/413, 416, 832, 833, 530/387, 366, 361, 362, 360

[56] References Cited

U.S. PATENT DOCUMENTS 4,436,658 3/1989 Peyrouset et al. .................. 530/832
4,816,252 3/1989 Stott et al. .......................... 530/833

OTHER PUBLICATIONS

Labib et al. J. Biol Chem vol. 251: No. 7 pp. 1969–1974, 1976, Bovine Secretory Component.
Chemical Abstracts, vol. 115, No. 1 (Jul. 9, 1991), Abstract No. 7255P.
Chemical Abstracts, vol. 84, No. 21 (May 24, 1976), Abstract No. 149069W.
J. Biol. Chem. 1976, 251(7), pp. 1969–1974 (1976).
Chemical Abstracts, vol. 101, No. 13 (Sep. 24, 1984), Abstract No. 106741M.
Chemical Abstracts, vol. 101, No. 13 (Sep. 24, 1984), Abstract No. 147060G.

Primary Examiner—Merrell C. Cashion, Jr.
Assistant Examiner—P. Lynn Touzeau
Attorney, Agent, or Firm—Millen, White, Zelano, and Branigan

[57] ABSTRACT

A secretory component-containing composition which is obtainable by contacting a milk or a whey with a cation exchange resin to allow the resin to absorb a secretory component contained in the milk or the whey and then eluting the secretory component and which has the following properties:

(a) contains a secretory component with the purity of at least 20% by weight,
(b) contains, besides the secretory component, at least an immunoglobulin and/or a serum albumin, and
(c) has anti-infectious effects.

9 Claims, No Drawings

SECRETORY COMPONENT-CONTAINING COMPOSITION

BACKGROUND OF THE INVENTION a) Field of the Invention

The present invention relates to a secretory component-containing composition separated from a milk or a whey.

The secretory component-containing composition of the present invention has anti-infectious effects and accordingly are useful in fields such as drugs, foods, cosmetics, feeds and the like.

b) Description of the Prior Art

A secretory component (hereinafter referred to as SC) is a glycoprotein synthesized in mammary glands and secreted into milk, and combines with immunoglobulin A (hereinafter referred to as IgA) which is one of immunoglobulins. The IgA which has combined with SC, is called secretory immunoglobulin A (hereinafter referred to as SIgA) and is contained in milk, particularly human milk in a relatively large amount. SIgA is the most important anti-infectious factor to babies, is not easily digested in the gastrointestinal tracts by protease, etc., and takes part in immune defense system by showing, for example, an agglutination action for antigens. This protease resistance of SIgA is known to be imparted by SC. Thus, SC plays an important role in the immune defense system in the body. Under such circumstances, there have long been made attempts to isolate SC from milk and examine the physical and chemical or biochemical properties. There are known various methods for isolating SC from milk. They include a method of first obtaining SIgA by DEAE type ion exchange chromatography and CM type ion exchange chromatography and then reducing the SIgA to obtain SC [e.g. K. Kobayashi, Immunochemistry, 8, 785-800 (1971)], and a method of obtaining free SC inherently present in milk. As the latter method, there are known (1) a method of subjecting a whey to ammonium sulfate fractionation and DEAE type ion exchange chromatography and then subjecting the unadsorbed whey portion to gel filtration chromatography, CM type ion exchange chromatography or phosphorylated ion exchange resin chromatography [J. E. Butler, Journal of Dairy Science, 55, 151-163 (1972); K. Kobayashi, Immunochemistry, 8, 785-800 (1971); R. S. Labib et al., Journal of Biological Chemistry, 251, 1969-1974 (1976)], (2) a method of subjecting a whey to DEAE type ion exchange chromatography, eluting the adsorbed component with a 0.01 M phosphate buffer solution of pH 7.6, and subjecting the eluate to CM type ion exchange chromatography [Enomoto et al., Digestive Organ and Immunity, 16, 146-150 (1986)], (3) a method of subjecting a whey to IgM-immobilized affinity chromatography [B. J. Underdown et al., Immunochemistry, 14, 111-118 (1977)], and methods which are slight modifications of the above methods (1) to (3).

In these methods, however, SC is isolated and purified only on laboratory basis, and there has not yet been proposed any method enabling the industrial production of SC-containing composition. The conventional methods have had further problems. That is, the whey from which SC has been removed by ammonium sulfate fractionation is difficult to find utilization; the DEAE type ion exchange chromatography requires a large amount of an ion exchange resin and is not suitable for industrial application; the gel filtration chromatography is not suitable for industrial application, either; the IgM-immobilized affinity chromatography is expensive, has restriction in washing and sterilization, and is not suitable at all for industrial application.

SUMMARY OF THE INVENTION

In view of the above situation, the present inventors made study to obtain a safe and inexpensive SC-containing composition using a milk or a whey as a material and found a SC-containing composition of the present invention.

The object of the present invention resides in providing a safe SC-containing composition of high SC concentration which is obtainable on an industrial scale and yet by simple treatments.

The SC-containing composition of the present invention is obtainable by (1) contacting a milk or a whey with a cation exchange resin to allow the resin to adsorb a SC contained in the milk or the whey and then eluting the SC, or (2) contacting a milk or a whey each adjusted to a pH of 6-9, with a cation exchange resin to allow the resin to adsorb a SC contained in the milk or the whey and then eluting the SC, or (3) contacting a milk or a whey each subjected to desalting so as to give conductivity of 5 mS/cm or less, with a cation exchange resin to allow the resin to adsorb a SC contained in the milk or the whey and then eluting the SC, or (4) contacting a milk or a whey each subjected to removal of lactoferrin and/or lactoperoxidase and then to desalting so as to give conductivity of 5 mS/cm or less, with a cation exchange resin to allow the resin to adsorb a SC contained in the milk or the whey and then eluting the SC, or (5) contacting a milk or a whey each subjected to removal of lactoferrin and/or lactoperoxidase and then to desalting so as to give conductivity of 5 mS/cm or less, with a cation exchange resin to allow the resin to adsorb a SC contained in the milk or the whey, eluting the SC, subjecting the eluate to desalting so as to give conductivity of 3 mS/cm or less, contacting the resulting material with an anion exchange resin, and recovering a SC from the fraction not adsorbed by the anion exchange resin.

According to the above procedure, there can be obtained a SC-containing composition (a) containing a SC with the purity of at least 20%, (b) containing, besides the SC, at least an immunoglobulin and/or a serum albumin, and (c) having anti-infectious effects.

DETAILED DESCRIPTION OF PREFERRED EMBODIMENTS

Detailed description is made hereinafter on preparation of the SC-containing composition of the present invention.

As the material for obtaining a SC-containing composition, there is used a milk or a whey derived from a mammal such as man, cow, buffalo, sheep, goat or the like. The milk may be a whole milk, but is preferably a nonfat milk because the fat contained in a whole milk adheres to the ion exchange resin used, leading to reduction in amount and concentration of SC in composition obtained. As the whey, there can be used a whey obtained by adjusting a milk to pH 4.6 to precipitate and remove caseins contained therein, or a whey obtained in the process of cheese production. Such a whey is desirable because it does not contain casein miscelles that sometimes clog the ion exchange resin used and enables easy washing.

In contacting a milk or a whey with a cation exchange resin to allow the resin to adsorb a SC contained in the milk or the whey, the pH of the milk or the whey is preferably 6-9. When the pH of the milk or the whey is lower than 6, there arises precipitation of a casein present in the milk, which is not preferable. When the pH of the whey is lower than 6, the cation exchange resin adsorbs, besides SC, impurities such as β-lactoglobulin, α-lactoalbumin, serum albumin, immunoglobulin and the like, resulting in a SC purity of less than 20%. When the pH of the milk or the whey is higher than 9, the amount of SC and other proteins adsorbed by the resin is lower, resulting in reduction in amount of SC recovered. Thus, in order to obtain a composition containing a SC with the purity of 20% or higher, it is preferable to adjust a milk or a whey to pH 6-9 when the milk or the whey is contacted with a cation exchange resin to allow the resin to adsorb a SC contained in the milk or the whey.

The SC-containing composition of the present invention is prepared by different methods depending upon the SC purity in desired final product.

When there is prepared a SC-containing composition containing a SC with the purity of 20% to lower than 50%, the composition can be obtained by contacting a milk or a whey with a cation exchange resin to allow the resin to adsorb a SC contained in the milk or the whey. In this case, the pH of the milk or the whey is adjusted to about 6-9.

When there is prepared a SC-containing composition containing a SC with the purity of 50% to lower than 70%, the composition can be obtained in the same manner as above except that there is used, as the material, a milk or a whey each subjected to desalting so as to give a conductivity of 5 mS/cm or less, preferably 2 mS/cm or less. Incidentally, the desalting for milk or whey is carried out by the electrodialysis, ultrafiltration, reverse osmosis, ion exchange chromatography, gel filtration, or the like. The amount of SC recovered and the purity of SC in the final product depend upon the degree of this desalting. Use of a material having conductivity of higher than 5 mS/cm gives the SC purity of less than 50%.

When there is prepared a SC-containing composition containing a SC with the purity of 70% to lower than 80%, there is used, as the material, a milk or a whey subjected to removal of lactoferrin (hereinafter referred to as LF) and/or lactoperoxidase (hereinafter referred to as LPO) and then to desalting so as to give conductivity of 5 mS/cm or less, preferably 2 mS/cm or less. The removal of LF and/or LPO can be effected by, for example, a method using a column in which a monoclonal antibody to LF has been immobilized [Japanese Patent Application Kokai (Laid-Open) No. 145200/1986]or a method of contacting a milk with sulfonated polysaccharide resins [Japanese Patent Application Kokai (Laid-Open) No. 255300/1988]. Use of a material subjected to removal of LF and/or LPO gives the SC purity of 70% or higher.

In the present invention, as the cation exchange resin used for adsorption of SC, there can be used cation exchange resins obtained by introducing a carboxymethyl group, a sulfuric acid group, a sulfopropyl group, a phosphoric acid group or the like into a cross-linked polysaccharide or cellulose or an acrylamide resin. Specific examples of the cation exchange resin include CM-Cellulofine C-500 having a carboxymethyl group (a product of Seikagaku Kogyo K. K.), Sulfonated Chitopearl having a sulfonic acid group (a product of Fuji Spinning Co., Ltd.), SP-Sephadex having a sulfopropyl group (a product of Pharmacia) and Phosphocellulose having a phosphoric acid group (a product of Pharmacia). When Sulfonated Chitopearl is used, its contact with a milk or a whey each not subjected to desalting results in low adsorption of SC, but the contact with a milk or a whey subjected to desalting enables adsorption of substantially all SC. The method for contacting a milk or a whey with a cation exchange resin includes, for example, a method wherein a milk or a whey is contacted with a cation exchange resin in a tank, a method wherein a milk or a whey is passed through a column packed with a cation exchange resin, and a method using a rotary column reactor [Japanese Patent Application Kokai (Laid-Open) No. 138295/1987]. When a SC-containing composition is prepared in a large amount, use of a rotary column reactor is efficient. The temperature at which a milk or a whey is contacted with a cation exchange resin, is not particularly restricted; however, the contact is usually made in a temperature range of 4° C. to less than 60° C. When the contact is made at temperatures lower than 4° C., there occur freezing or viscosity increase of material, separation of fat, etc. When the contact is made at temperatures of 60° C. or more, there occurs denaturation of SC in some cases. Since the propagation of microorganisms is striking at temperatures of 15° C. or more, the treatment of material in a large amount is desirably made at temperatures lower than 15° C. In this case, it is desirable that 1 kg of a material be mixed with about 1-100 g of a cation exchange resin and the mixture be stirred for about 15 minutes to about 6 hours.

In eluting the adsorbed SC, there is used a salt solution having an ionic strength of 0.005-0.25 and a pH of 6-9. When the ionic strength is lower than 0.005, the adsorbed SC cannot be eluted from the resin containing the adsorbed SC. When the ionic strength is higher than 0.25, the impurities adsorbed by the resin are also eluted from the resin together with the adsorbed SC, resulting in reduced SC purity in the final product. The type of the salt used for elution of SC is not particularly restricted, but is exemplified by sodium chloride, potassium chloride, etc.

The cation exchange resin used for adsorption and elution of SC can be reused by washing with a salt solution having an ionic strength higher than 0.25, followed by thorough washing with water.

The SC obtained by elution is subjected, as necessary, to concentration, desalting and drying. The concentration can be effected by means of vacuum concentration, ultrafiltration, reverse osmotic pressure filtration or the like. The desalting can be effected by the use of ultrafiltration, dialysis, electrodialysis, ion exchange chromatography, gel filtration, or the like. The drying can be effected by means of freeze-drying, spray drying or the like.

When there is prepared a SC-containing composition containing a SC with the purity of 80% or higher, a milk is subjected to removal of LF and/or LPO and then to desalting so as to give conductivity of 5 mS/cm or less, preferably 2 mS/cm or less; the resulting material is contacted with a cation exchange resin to allow the resin to adsorb a SC contained in the material; the adsorbed SC is eluted; the eluate (SC-containing fraction) is contacted with an anion exchange resin to allow the resin to adsorb impurities contained in the SC-containing fraction. That is, the SC-containing fraction obtained by the cation exchange resin treatment is desalted so as to give conductivity of 3 mS/cm or less, preferably 1 mS/cm or less; the resulting fraction is contacted with an anion exchange resin; the unadsorbed fraction and/or the fraction which has been adsorbed by the resin and then eluted by an aqueous solution having an ionic strength lower than 0.005 is recovered, whereby a SC-containing composition containing a SC with the purity of 80% or higher is obtained. When the conductivity of the SC-containing fraction is more than 3 mS/cm, it is difficult to allow the anion exchange resin to adsorb impurities and, as a result, the contact of said fraction with the anion exchange resin is unable to achieve the elevation of SC purity. Specific examples of the anion exchange resin usable in the present invention include resins having a tertiary or quaternary amine, for example, DEAE-Sepharose FF (a product of Pharmacia) and Q-Sepharose FF (a product of Pharmacia). The contact with the anion exchange resin can be effected in the same manner as in the contact with the cation exchange resin.

The SC-containing composition of the present invention can be used as feeds when the SC purity therein is about 20% and, as the purity becomes higher, can be used as a material for foods, beverages, cosmetcis, drugs, etc.

The anion exchange resin after use can be reused by washing with a salt solution having an ionic strength higher than 0.2, followed by thorough washing with water.

Meanwhile, the milk or the whey from which the SC has been removed can be used as it is, as a material for foods, beverages, cosmetcis, drugs, etc.

According to the present invention, there can be obtained a SC-containing composition:

(a) containing a SC with the purity at least 20%, (b) containing, besides the SC, an immunoglobulin and/or a serum albumin, and (c) having anti-infectious effects. This SC-containing composition containing a SC in a high concentration can be obtained by a simple procedure which comprises contacting a milk directly with a cation exchange resin to allow the resin to adsorb a SC contained in the milk and eluting the adsorbed SC with a salt solution. In the present invention, since the SC concentration in material milk is low (0.01–0.05 g/kg) as compared with the whey protein concentration (30 g/kg), the amount of cation exchange resin used can be small as compared with the conventional method of firstly subjecting a milk to a pretreatment for adsorption and removal of whey proteins by an anion exchange resin; a large amount of milk can be treated in a short period of time; accordingly, a larger amount of SC-containing composition can be obtained. Further, in obtaining a large amount of a SC-containing composition according to the conventional method, a large amount of an anion exchange resin, large-sized facilities and consequently expensive production cost were required; meanwhile, in the present invention, the amount of anion exchange resin can be small, no large-sized facility is required, and the cost for obtaining a SC-containing composition can be reduced.

Thus, the present invention makes it possible to obtain a SC-containing composition containing a SC in a high concentration, in simplified steps in a large amount at the inexpensive production costs with a low facility investment. The SC-containing composition obtained in the present invention has no safety problem because the present invention uses, as auxiliary materials, only salts such as sodium chloride and the like; contains impurities in a small amount; contains an immunoglobulin and a serum albumin; and has anti-infectious effects. The SC-containing composition can be used as a feed or a material for foods, drugs and cosmetics, depending upon the SC purity in composition.

In the present invention, the fraction of a material milk not adsorbed by a cation exchange resin, as well as the fraction adsorbed by the cation exchange resin and, after elution with an aqueous salt solution, adsorbed by an anion exchange resin contain a whey, milk proteins, etc. in large amounts; as the auxiliary materials, there are used only water and salts; therefore, the above two fractions can be used as a material for foods (e.g nonfat milk), whereby the material milk can be used efficiently.

Next, there is described the anti-infectious test conducted for the SC-containing composition of the present invention.

As the test animals, there were used 20 Wistar male rats each weighing about 200 g. They were divided into four groups each consisting of 5 such rats. One of the four groups was used as a control group and the remaining three groups were used as test groups. To the rats of test groups was forcibly administered, by means of an oral sonde, a SC-containing composition in an amount of 0.05 mg/day, 0.1 mg/day or 1 mg/day in terms of SC. Then, to all the rats (the control group and the test groups) was orally administered a given amount of a pathogenic Escherichia coli, ATCC 12014, after which the incidence of diarrhea in the rats was examined. The results are shown in Table 1.

TABLE 1

| Sample | Incidence of diarrhea (%) |
| --- | --- |
| Control group | 100 |
| Test groups administered with SC-containing composition | |
| 0.05 mg/day | 80 |
| 0.1 mg/day | 40 |
| 1 mg/day | 0 |

The present invention is hereinafter described specifically with reference to Examples.

EXAMPLE 1

Raw whole milk was defatted by centrifugation and the resulting fresh nonfat milk was adjusted to pH 4.6 to precipitate and remove caseins present in the milk, whereby a whey was obtained. The whey (12.4 kg) was adjusted to pH 6.2 with sodium hydroxide and then stirred with 100 g of CM-Cellulofine C-500 (a product of Seikagaku Kogyo K.K.) in a tank for 1 hour to allow the resin to adsorb a SC-containing fraction of the whey. The supernatant liquor was removed by decantation and the resin containing the adsorbed SC-containing fraction was packed into a packed bed type column (3×30 cm). Water was passed through the column to thoroughly wash the resin, and a 0.14 M aqueous sodium chloride solution was passed to further wash the resin. Then, 500 ml of a 0.2 M aqueous sodium chloride solution was passed to elute the SC-containing fraction. The eluate was concentrated to 50 ml by the use of a rotary evaporator. The concentrate was subjected to dialysis against deionized water to remove salts present in the concentrate. The desalted concentrate was freeze-dried to obtain 6 mg of a SC-containing composition. The SC purity was 52% when measured by SDS-polyacrylamide gel electrophoresis, and the remainder was occupied by 42% of an immunoglobulin and 6% of a serum albumin.

EXAMPLE 2

A whey obtained in the production of cheese from a goat milk was freeze-dried to obtain 3.5 kg of a freeze-dried whey. It was dissolved in 31.5 kg of water. The resulting solution of pH 6.1 was passed through a column (3×30 cm) packed with 200 g of CM-Cellulofine C-500 (a product of Seikagaku Kogyo K.K.), at a flow rate of 7 l/hr to allow the resin to adsorb a SC-containing fraction of the whey. Water was passed through the column to thoroughly wash the resin, and then 2 l of a 0.13 M aqueous sodium chloride solution was passed to further wash the resin. 2 l of a 0.25 M aqueous sodium chloride solution was passed to elute the SC-containing fraction. The eluate was desalted by the use of an ultrafilter membrane (molecular weight cutoff: 50,000), and then concentrated to 500 ml by the use of a rotary evaporator. The concentrate was freeze-dried to obtain 108 g of a SC-containing composition. The SC purity was 47% when measured by SDS-polyacrylamide gel electrophoresis.

EXAMPLE 3

400 ml of a cheese whey of pH 6.2 was desalted by the use of an ultrafilter membrane (molecular weight cutoff: 10,000) so as to give conductivity of 1 mS/cm or less. The desalted whey was passed through a column (1.3×15 cm) packed with CM-Cellulofine C-500 (a product of Seikagaku Kogyo K.K.), at a flow rate of 3 ml/min to alow the resin to adsorb a SC-containing fraction of the whey. A phosphate buffer solution having an ionic strength of 0.004 and a pH of 7.0 was passed through the column to wash the resin. Then, a phosphate buffer solution having an ionic strength of 0.034 and a pH of 7.0 was passed through the column to elute the SC-containing fraction. The eluate was concentrated by the use of an ultrafilter membrane (molecular weight cutoff: 10,000) and the concentrate was freeze-dried to obtain 24 mg of a SC-containing composition. The SC purity was 62% when measured by SDS-polyacrylamide gel electrophoresis.

EXAMPLE 4

500 ml of a nonfat milk of pH 6.7 was desalted by the use of an ultrafilter membrane (molecular weight cutoff: 10,000) so as to give conductivity of 3 mS/cm. The desalted nonfat milk was passed through a column (1.3×15 cm) packed with 12 ml of Sulfonated Chitopearl (a product of Fuji Spinning Co., Ltd.), at a flow rate of 3 ml/min, to allow the resin to adsorb a SC-containing fraction of the nonfat milk. A deionized water was passed through the column to wash the resin, and then an aqueous sodium chloride solution having an ionic strength of 0.07 was passed to elute the SC-containing fraction. The eluate was concentrated by the use of an ultrafilter membrane (molecular weight cutoff: 20,000). The concentrate was freeze-dried to obtain 32 mg of a SC-containing composition. The SC purity was 64% when measured by SDS-polyacrylamide gel electrophoresis.

EXAMPLE 5

20 l of a cheese whey was adjusted to pH 8.0 and then stirred with 500 ml of SP-Sephadex (a product of Pharmacia) in a tank at 4° C. for 8 hours to allow the resin to adsorb a SC-containing fraction of the whey. The resulting gel was recovered and packed into a column (5.8×30 cm). Water was passed through the column to thoroughly wash the resin, and then a Tris-hydrochloric acid buffer solution having an ionic strength of 0.001 and a pH of 8.0 was passed to wash the resin. Thereafter, a 10 mM Tris-hydrochloric acid buffer solution containing potassium chloride, having an ionic strength of 0.10 and a pH of 8.0 was passed to elute the SC-containing fraction. The eluate was desalted by the use of an ion exchange resin for desalting, Amberlite MB-3 (a product of Organo Co., Ltd.) so as to give conductivity of 0.6 mS/cm and then concentrated. The concentrate was freeze-dried to obtain 167 mg of a SC-containing composition. The SC purity was 46% when measured by SDS-polyacrylamide gel electrophoresis.

EXAMPLE 6

400 kg of a fresh nonfat milk was circulated through a rotary column reactor (a product of Tokyo Rika Kikai Co., Ltd.) packed with 1.7 l of Sulfonated Chitopearl (a product of Fuji Spinning Co., Ltd.) at a flow rate of 200 l/hr for 2 hours. Then, water was passed through the column reactor to thoroughly wash the resin, after which 60 l of a 1.0 M aqueous sodium chloride solution was passed to elute a LF fraction of the nonfat milk. This LF fraction was desalted and concentrated by the use of an ultrafilter membrane (molecular weight cutoff: 50,000). The concentrate was freeze-dried to obtain a LF powder. Meanwhile, the portion of the nonfat milk containing no LF fraction was circulated through a rotary column reactor (a product of Tokyo Rika Kikai K.K.) packed with 1.7 l of SP-Sephadex (a product of Pharmacia), at a flow rate of 200 l/hr for 4 hours. Water was passed through the column reactor to thoroughly wash the resin, and 60 l of a 0.13 M aqueous sodium chloride solution was passed to further wash the impurities adsorbed by the resin. Thereafter, 60 l of a 0.22 M aqueous sodium chloride solution was passed to elute a SC containing-fraction of the nonfat milk. The eluate was desalted and concentrated by the use of an ultrafilter membrane (molecular weight cutoff: 50,000). The concentrate was stirred and contacted with 200 g of DEAE-Cellulofine (a product of Seikagaku Kogyo Co., Ltd.) for 30 minutes. The mixture was filtered through a filter cloth to remove the resin and obtain a supernatant liquor. The liquor was freeze-dried to obtain 9.5 g of a SC-containing composition. The SC concentration in composition was 82% when measured by SDS-polyacrylamide gel electrophoresis. Incidentally, the nonfat milk as a material was a powdered nonfat milk obtained by sterilizing and spray-drying a liquid nonfat milk.

EXAMPLE 7

200 l of a nonfat milk having a pH of 6.4 and conductivity of 6 mS/cm was circulated through a rotary column reactor (a product of Tokyo Rika Kikai Co., Ltd.) packed with 1.7 l of Sulfonated Chitopearl (a product of Fuji Spinning Co., Ltd.), at a flow rate of 200 l/hr for 2 hours to remove LF and LPO from the nonfat milk. (The rotary column reactor had to be used in the later adsorption and elution of SC-containing fraction, therefore, was renewed by (1) passing water to thoroughly wash the resin, (2) passing a 0.7 M aqueous sodium chloride solution to elute the LF and the LPO and (3) passing water.) Meanwhile, the LF- and LPO-removed nonfat milk was desalted by the use of an electrodialysis membrane so as to give conductivity of 1.5 mS/cm and then circulated through the rotary column reactor used for the removal of LF and LPO, at a flow rate of 200 l/hr for 4 hours to allow the resin in the reactor to adsorb a SC-containing fraction of the nonfat milk. Water was passed through the rotary column reactor to thoroughly wash the resin, and then an aqueous sodium chloride solution having an ionic strength of 0.003 was passed to further wash the resin. Thereafter, an aqueous sodium chloride solution having an ionic strength of 0.2 was passed to elute the SC-containing fraction. Further, a 1 M aqueous sodium chloride solution was passed to wash the resin, and then water was passed to thoroughly wash the resin. 60 l of the eluate was concentrated to 2 l by the use of an ultrafilter membrane (molecular weight cutoff: 50,000), and the concentrate was desalted by the use of an electrodialysis membrane so as to give conductivity of 0.3 mS/cm and freeze-dried to obtain 5.1 g of a SC-containing composition. The SC purity was 79% when measured by SDS-polyacrylamide gel electrophoresis.

EXAMPLE 8

The SC-containing fraction obtained in Example 7 was purified using an anion exchange resin. The SC-containing fraction was passed through a column (5.8×30 cm) packed with 500 ml of DEAE-Sephalose CL-6B (a product of Pharmacia) and then equilibrated with a phosphate buffer solution having an ionic strength of 0.001 and a pH of 7.0, at a flow rate of 3 ml/min to recover a non-adsorbed fraction of the SC-containing fraction. The non-adsorbed fraction was concentrated and freeze-dried to obtain 3.9 g of a SC-containing composition. The SC purity was 88% when measured by SDS-polyacrylamide gel electrophoresis. Further, a phosphate buffer solution having an ionic strength of 0.01 and a pH of 7.0 was passed through the column to elute a fraction adsorbed by the anion exchange resin. The eluate was concentrated, and the concentrate was dialyzed against deionized water for two nights. The retentate was freeze-dried to obtain 0.8 g of a SC-containing composition. The SC purity was 82% when measured by SDS-polyacrylamide gel electrophoresis.

We claim:

1. A production process of a secretory component-containing composition which contains a secretory component with a purity of at least 70% and which has anti-infectious effects, comprising the steps of:
    (a) subjecting a milk or whey to chromatography to remove lactoferrin and lactoperoxidase therefrom;
    (b) desalting the resultant milk or whey so as to give a conductivity of up to 5 mS/cm;
    (c) treating the desalted milk or whey with a cation exchange resin to allow the resin to adsorb a secretory component contained in the milk or whey; and
    (d) eluting the secretory component adsorbed by the resin using a salt solution having an ionic strength of 0.005 to 0.25 and a pH of 6 to 9, so that the secretory component can be recovered from the eluate at a purity of 70% or more.

2. A production process of a secretory component-containing composition which contains a secretory component with a purity of at least 80% and which has anti-infectious effects, comprising the steps of:
    (a) subjecting a milk or whey to chromatography to remove lactoferrin and lactoperoxidase therefrom;
    (b) desalting the resultant milk or whey so as to give a conductivity of up to 5 mS/cm;
    (c) treating the desalted milk or whey with a cation exchange resin to allow the resin to adsorb a secretory component contained in the milk or whey; and
    (d) eluting the secretory component adsorbed by the resin using a salt solution having an ionic strength of 0.005 to 0.25 and a pH of 6 to 9;
    (e) desalting the eluate so as t give a conductivity of up to 3 mS/cm; and
    (f) passing the desalted eluate through an anion exchange resin, so that the secretory component can be recovered from the passed eluate at a purity of 80% or more.

3. A process according to claim 1, wherein the chromatography is conducted employing a column wherein a monoclonal antibody to lactoferrin is immobilized.

4. A process according to claim 1, wherein the chromatography is conducted employing a sulfonated polysaccharide resin.

5. A process according to claim 1, wherein the milk or whey is contacted with a cation exchange resin at a temperature of 4° C. to 60° C.

6. A process according to claim 1, wherein the cation exchange resin is obtained by introducing the carboxymethyl group, sulfuric acid group, sulfopropyl group or phosphoric acid group into crosslinked polysaccharide or cellulose and polyacrylamide resin.

7. A process according to claim 2, wherein the anion exchange resin is a tertiary or quaternary amine.

8. A process according to claim 1, wherein the conductivity of the desalted milk or whey is 2 mS/cm.

9. A process according to claim 1, wherein the chromatography is conducted employing a sulfonated polysaccharide resin; wherein the milk or whey is contacted with a cation exchange resin at a temperature of 4° C. to 60° C.; wherein the cation exchange resin is obtained by introducing the carboxymethyl group, sulfuric acid group, sulfopropyl group or phosphoric acid group into crosslinked polysaccharide or cellulose and polyacrylamide resin; and which comprises the further steps of:
    (e) desalting the eluate so as to give a conductivity of up to 3 mS/cm; and
    (f) passing the desalted eluate through an anion exchange resin, so that the secretory component can be recovered from the passed eluate at a purity of 80% or more.

* * * * *

UNITED STATES PATENT AND TRADEMARK OFFICE
CERTIFICATE OF CORRECTION

PATENT NO. : 5,179,197

DATED : January 12, 1993

INVENTOR(S) : Toshiaki UCHIDA et al.

It is certified that error appears in the above-identified patent and that said Letters Patent is hereby corrected as shown below:

On the title page item [75]:

Please change the third inventors' name to read --

Shunichi DOSAKO.

Signed and Sealed this

Twenty-third Day of November, 1993

Attest:

BRUCE LEHMAN

*Attesting Officer*  *Commissioner of Patents and Trademarks*